US011234701B2

(12) United States Patent
Pribanic et al.

(10) Patent No.: US 11,234,701 B2
(45) Date of Patent: Feb. 1, 2022

(54) POWERED SURGICAL TACK APPLIER

(71) Applicant: Covidien LP, Mansfield, MA (US)

(72) Inventors: Russell Pribanic, Roxbury, CT (US); Christopher Switalski, Glastonbury, CT (US); David A. Zeichner, Oxford, CT (US); David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 225 days.

(21) Appl. No.: 16/532,534

(22) Filed: Aug. 6, 2019

(65) Prior Publication Data
US 2020/0093492 A1    Mar. 26, 2020

Related U.S. Application Data

(60) Provisional application No. 62/734,290, filed on Sep. 21, 2018.

(51) Int. Cl.
*A61B 17/10* (2006.01)
*A61B 90/00* (2016.01)
(Continued)

(52) U.S. Cl.
CPC .............. *A61B 17/10* (2013.01); *A61B 90/08* (2016.02); *A61F 2/0063* (2013.01);
(Continued)

(58) Field of Classification Search
CPC ..... A61B 17/068; A61B 17/064; A61B 17/10; A61B 2017/00017; A61B 2017/00119;
(Continued)

(56) References Cited

U.S. PATENT DOCUMENTS 5,810,882 A    9/1998 Bolduc et al.
5,824,008 A    10/1998 Bolduc et al.
(Continued)

FOREIGN PATENT DOCUMENTS

EP    1382302 B1    3/2009
EP    1908409 B1    12/2010
(Continued)

OTHER PUBLICATIONS

Extended European Search Report issued in European Patent Application No. 19198755.1, dated Feb. 18, 2020.
(Continued)

*Primary Examiner* — Melanie R Tyson
*Assistant Examiner* — Paige A Codrington
(74) *Attorney, Agent, or Firm* — Carter, DeLuca & Farrell LLP

(57) ABSTRACT

A handle assembly for use with a surgical tack applier includes an actuation assembly and an articulation lever assembly configured to articulate an articulation portion of the surgical tack applier. The actuation assembly includes a motor, an actuation rod, and an actuation switch configured to actuate the motor. The actuation rod has a first end operatively coupled to an output shaft of the motor for concomitant rotation therewith, and a second end operatively coupled to a loading unit of the surgical tack applier such that rotation of the actuation rod ejects a surgical tack from the loading unit. The articulation lever assembly includes an articulation rod operatively coupled with an articulation portion of the surgical tack applier such that axial displacement of the articulation rod causes articulation of the articulation portion, and an articulation lever operatively coupled with the articulation rod.

22 Claims, 5 Drawing Sheets

(51) Int. Cl.
*A61F 2/00* (2006.01)
*A61B 17/00* (2006.01)

(52) U.S. Cl.
CPC .............. *A61B 2017/00017* (2013.01); *A61B 2017/00057* (2013.01); *A61B 2017/00128* (2013.01); *A61B 2017/00398* (2013.01); *A61B 2017/00402* (2013.01); *A61B 2017/00424* (2013.01); *A61B 2017/00734* (2013.01); *A61B 2090/0803* (2016.02); *A61F 2002/0072* (2013.01)

(58) Field of Classification Search
CPC ........ A61B 2017/00398; A61B 17/072; A61B 17/07207–07292; A61B 2017/0641–0647; A61F 2/0063; A61F 2/0095; A61F 2002/0072; A61F 2220/0016
USPC ....................................................... 606/151
See application file for complete search history.

(56) References Cited

U.S. PATENT DOCUMENTS

| | | | |
|---|---|---|---|
| 5,830,221 | A | 11/1998 | Stein et al. |
| 7,867,252 | B2 | 1/2011 | Criscuolo et al. |
| 8,282,670 | B2 | 10/2012 | Shipp |
| 8,414,627 | B2 | 4/2013 | Corradi et al. |
| 8,556,930 | B2 | 10/2013 | Ellingwood |
| 9,445,814 | B2 | 9/2016 | Ranucci et al. |
| 9,510,825 | B2 | 12/2016 | Alexander et al. |
| 2003/0009441 | A1 | 1/2003 | Holsten et al. |
| 2004/0230208 | A1 | 11/2004 | Shayani |
| 2008/0086154 | A1 | 4/2008 | Taylor et al. |
| 2009/0118776 | A1 | 5/2009 | Kelsch et al. |
| 2010/0213240 | A1* | 8/2010 | Kostrzewski ...... A61B 17/3209 227/180.1 |
| 2011/0071578 | A1* | 3/2011 | Colesanti ............. A61B 17/064 606/305 |
| 2011/0087240 | A1 | 4/2011 | Shipp |
| 2011/0204119 | A1* | 8/2011 | McCuen .......... A61B 17/07207 227/175.1 |
| 2011/0295282 | A1 | 12/2011 | Glick et al. |
| 2012/0271285 | A1* | 10/2012 | Sholev ................. A61B 17/068 606/1 |
| 2013/0018392 | A1 | 1/2013 | Zergiebel |
| 2013/0313305 | A1* | 11/2013 | Scirica ............. A61B 17/07207 227/180.1 |
| 2014/0012289 | A1* | 1/2014 | Snow ............ A61B 17/320016 606/130 |
| 2014/0088349 | A1 | 3/2014 | Alexander et al. |
| 2014/0121684 | A1 | 5/2014 | Criscuolo et al. |
| 2014/0276972 | A1* | 9/2014 | Abuzaina ............. A61B 17/068 606/143 |
| 2016/0166255 | A1 | 6/2016 | Fischvogt |
| 2018/0042591 | A1* | 2/2018 | Russo ................... A61B 17/00 |
| 2018/0049738 | A1* | 2/2018 | Meloul ................. A61B 17/068 |
| 2019/0200986 | A1* | 7/2019 | Shelton, IV .......... A61B 5/053 |
| 2020/0093492 | A1 | 3/2020 | Pribanic et al. |

FOREIGN PATENT DOCUMENTS

| | | |
|---|---|---|
| EP | 2684529 A2 | 1/2014 |
| EP | 2870924 A1 | 5/2015 |
| EP | 2870927 A1 | 5/2015 |
| EP | 2870929 A1 | 5/2015 |
| EP | 3195812 A1 | 7/2017 |
| WO | 9707744 A1 | 3/1997 |
| WO | 200176488 | 10/2001 |
| WO | 2013192107 A1 | 12/2013 |
| WO | 2014064695 A2 | 5/2014 |
| WO | 2016157171 A1 | 10/2016 |
| WO | 2016205183 A1 | 12/2016 |
| WO | 2017066732 A1 | 4/2017 |

OTHER PUBLICATIONS

Extended European Search Report EP14199642.1 dated Sep. 11, 2015.
Extended European Search Report issued in EP Application No. 20211932.7, dated May 28, 2021.

* cited by examiner

POWERED SURGICAL TACK APPLIER

CROSS-REFERENCE TO RELATED APPLICATION

This application claims the benefit of and priority to U.S. Provisional Patent Application No. 62/734,290 filed Sep. 21, 2018, the entire disclosure of which is incorporated by reference herein.

BACKGROUND

Technical Field

The present disclosure relates to surgical instruments and, more particularly, to a surgical tack applier for attaching a prosthesis in place in the repair of a defect in tissue such as an inguinal hernia.

Background of Related Art

Various surgical procedures require instruments capable of applying fasteners to tissue to form tissue connections or to secure objects to tissue. For example, during hernia repair it is often desirable to fasten a mesh to tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed outside the abdominal wall by suturing. The mesh is attached with sutures over the opening in the abdominal wall to provide reinforcement. However, this may also be accomplished through the use of minimally invasive surgical fasteners such as, e.g., surgical tacks.

Accordingly, a need exists for surgical tack appliers which include the ability for its loading unit to articulate, while inhibiting premature ejection of tacks and timing issues when attempting to eject tacks.

SUMMARY

The present disclosure describes a device for applying surgical tacks that demonstrates a practical approach to meeting the performance requirements and overcoming usability challenges associated with applying surgical tacks through a surgical mesh and into tissue.

In accordance with an embodiment of the present disclosure, a handle assembly for use with a surgical tack applier includes an actuation assembly and an articulation lever assembly. The actuation assembly includes a motor, an actuation rod, and an actuation switch configured to actuate the motor. In particular, the actuation rod has a first end operatively coupled to an output shaft of the motor for concomitant rotation therewith, and a second end operatively coupled to a loading unit of the surgical tack applier such that rotation of the actuation rod ejects a surgical tack from the loading unit. The articulation lever assembly is configured to articulate an articulation portion of the surgical tack applier. The articulation lever assembly includes an articulation rod operatively coupled with an articulation portion of the surgical tack applier such that axial displacement of the articulation rod causes articulation of the articulation portion, and an articulation lever operatively coupled with the articulation rod.

In an embodiment, the actuation assembly may further include a processor configured to control the motor.

In another embodiment, the actuation assembly may further include an optical motor encoder configured to count turns of the motor output shaft to ensure a proper number of turns are made to insert a surgical tack into tissue. The optical motor encoder may be operatively connected to the actuation rod and the processor.

In another embodiment, the actuation assembly may further include an encoder wheel configured to ensure correct clocking of a distal end of the actuation rod relative to the loading unit.

In yet another embodiment, the actuation assembly may further include a light emitting diode coupled with the processor to indicate status of ejection of the surgical tack from the loading unit.

In still yet another embodiment, the articulation rod may define a transverse bore dimensioned to receive a drive pin coupled with the articulation lever. The drive pin may define a bore dimensioned to receive the actuation rod therethrough.

In an embodiment, the handle assembly may further include a battery pack electrically coupled to the motor and the processor.

In an embodiment, the actuation assembly may further include a piezoelectric element configured to provide audible tone for proper ejection of the surgical tack from the loading unit.

In another embodiment, the handle assembly may further include a housing pivotably supporting the articulation lever.

In yet another embodiment, the articulation lever may include a housing portion and an engaging portion slidably disposed on an engaging surface of the housing.

In still yet another embodiment, the engaging surface may define an arcuate profile to enable sliding of the engaging portion in an arc.

In still yet another embodiment, the articulation lever assembly may include a biasing member configured to bias the engaging portion of the articulation lever away from the housing of the handle assembly.

In another embodiment, the housing may include a detent portion configured to secure a position of the articulation lever relative to the housing of the handle assembly.

In an embodiment, the articulation lever assembly may further include articulation pivot arms pivotably secured to the housing of the handle assembly. The articulation pivot arms may be configured to receive the biasing member therebetween.

In another embodiment, the articulation pivot arms may be received in the housing portion of the articulation lever.

In yet another embodiment, the articulation rod may define a lumen dimensioned to receive the actuation rod therethrough.

In accordance with another aspect of the present disclosure, a surgical tack applier includes a handle assembly and an elongate member. The handle assembly includes an actuation assembly and an articulation lever assembly. The actuation assembly includes a motor, an actuation rod having a first end operatively coupled to an output shaft of the motor for concomitant rotation therewith, and an actuation switch configured to actuate the motor. The articulation lever assembly includes an articulation rod and an articulation lever operatively coupled with the articulation rod. The elongate member extends distally from the handle assembly. The elongate member includes a loading unit having a plurality of surgical tacks, and an articulation portion configured to pivot with respect to a longitudinal axis defined by the elongate member. The articulation rod is operatively coupled with the articulation portion of the elongate member such that axial displacement of the articulation rod causes articulation of the articulation portion. A second end of the actuation rod is operatively coupled to the loading unit such that rotation of the actuation rod ejects a surgical tack from the loading unit. The actuation rod extends through the articulation rod.

In an embodiment, the actuation assembly may further include a processor configured to control the motor.

In another embodiment, the actuation assembly may further include an optical motor encoder configured to count turns of the motor output shaft to ensure a proper number of turns are made to insert a surgical tack into tissue. The optical motor encoder may be operatively connected to the actuation rod and the processor.

In another embodiment, the actuation assembly may include an encoder wheel configured to ensure correct clocking of a distal end of the actuation rod relative to the loading unit.

BRIEF DESCRIPTION OF THE DRAWINGS

Various aspects of the present disclosure are described hereinbelow with reference to the drawings, which are incorporated and constitute a part of this specification, wherein.

DETAILED DESCRIPTION OF EMBODIMENTS

Figure 1:
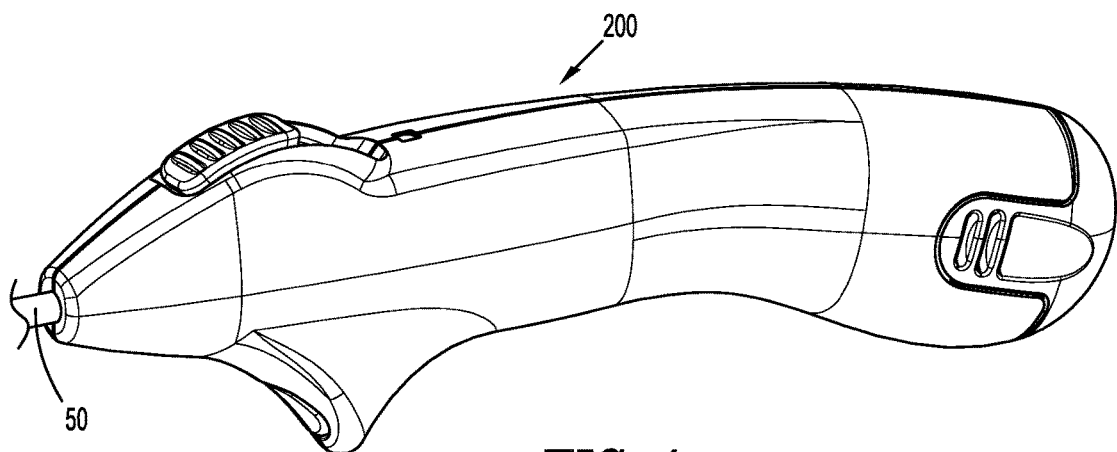
FIG. 1 is a perspective view of a handle assembly of a powered surgical tack applier in accordance with an embodiment of the present disclosure.

Embodiments of the presently disclosed surgical instrument are described in detail with reference to the drawings, in which like reference numerals designate identical or corresponding elements in each of the several views. As used herein, the term "distal," as is conventional, will refer to that portion of the instrument, apparatus, device, or component thereof which is farther from the user, while the term "proximal" will refer to that portion of the instrument, apparatus, device, or component thereof which is closer to the user. In the following description, well-known functions or constructions are not described in detail to avoid obscuring the present disclosure in unnecessary detail.

With reference to FIGS. 1-4, a handle assembly for use with a surgical tack applier for applying a surgical tack 10 suitable for insertion through a surgical mesh "M" and tissue "T" is shown generally as a handle assembly 200. The surgical tack applier generally includes the handle assembly 200, an elongate member 50 having an articulation portion 60, and a loading unit 30 selectably connectable to a distal end of the elongate member 50. The loading unit 30 is electro-mechanically coupled to the handle assembly 200 and supports a plurality of surgical tacks 10.

The loading unit 30 includes an outer tube 32 defining a lumen (not shown), a spiral or coil 36 fixedly disposed within the outer tube 32, and an inner tube 38 rotatably disposed within the coil 36. The inner tube 38 defines a lumen therethrough, and includes a first portion 38a and a splined second portion 38b. The second portion 38b of the inner tube 38 is slotted, defining a pair of tines $38b_1$ and a pair of channels $38b_2$. The second portion 38b of the inner tube 38 is configured to support the plurality of surgical tacks 10 within the inner tube 38. In particular, the surgical tacks 10 are loaded into the loading unit 30 such that the pair of opposing threaded sections 112a of the surgical tacks 10 extend through respective channels $38b_2$ of the second portion 38b of the inner tube 38 and are slidably disposed within the groove of the coil 36, and the pair of tines $38b_1$ of the second portion 38b of the inner tube 38 are disposed within the pair of slotted sections 116a of the surgical tack 10. In use, as the inner tube 38 is rotated about a longitudinal axis "X-X" thereof, relative to the coil 36, the pair of tines $38b_1$ of the inner tube 38 transmits the rotation to the surgical tacks 10 and advance the surgical tacks 10 distally as the head threads 114a of the surgical tacks 10 engage with the coil 36.

Figure 2:
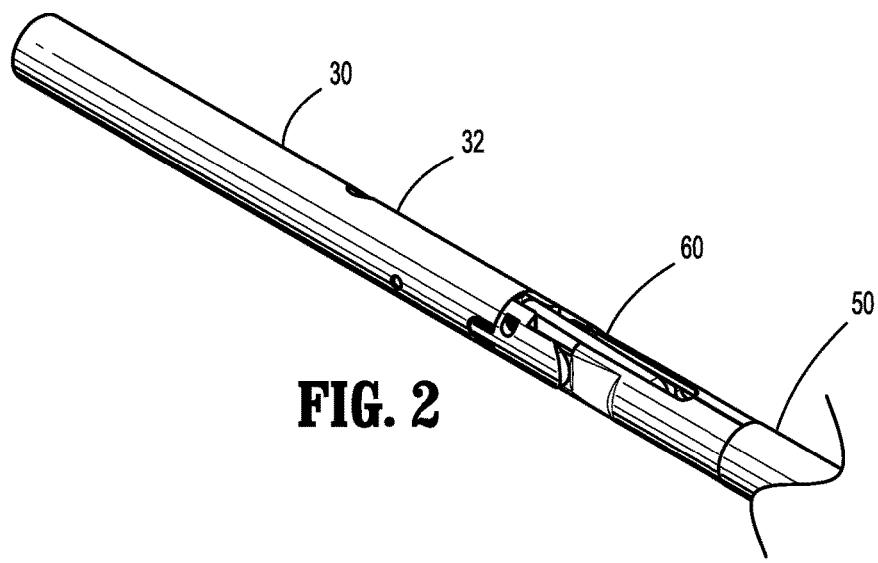
FIG. 2 is a partial perspective view of an elongate member of the powered surgical tack applier.
Figure 3:
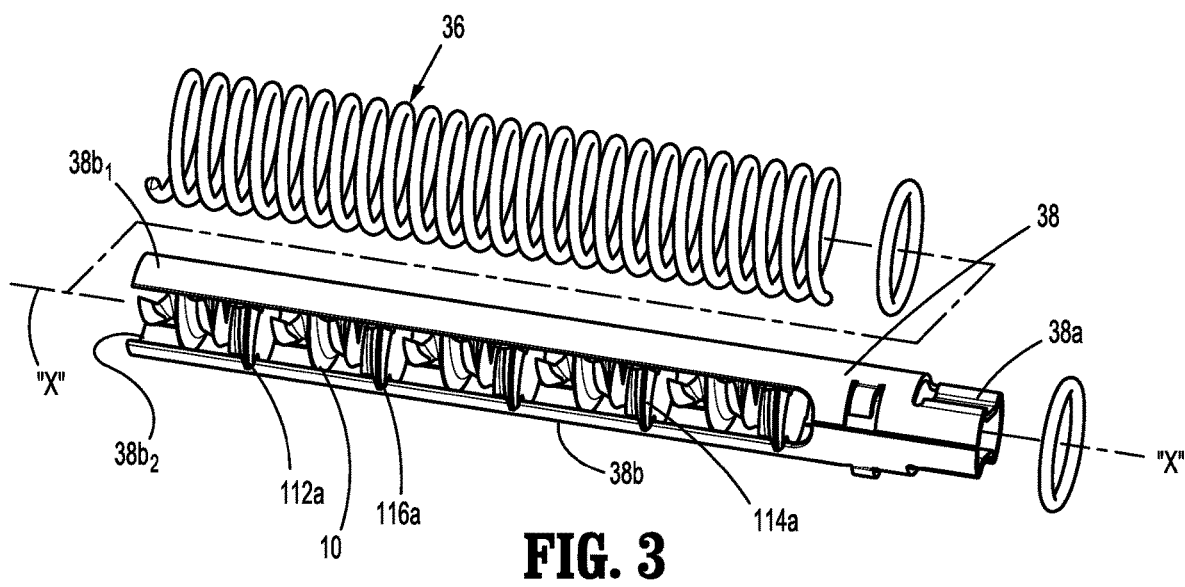
FIG. 3 is a partial perspective view of a loading unit of the surgical tack applier of FIG. 1, illustrating a coil separated from an inner tube.

With particular respect to FIG. 2, the surgical tack applier includes an articulation portion 60 operatively coupled with an articulation lever assembly 300 (FIG. 6) supported in the handle assembly 200. The articulation portion 60 may include a drive assembly (not shown) having a slidable tube and an articulation arm pivotally coupled to the slidable tube. The articulation lever assembly 300 is coupled to the slidable tube so that when the articulation lever assembly 300 is actuated the slidable tube is displaced through the elongated member 50. Longitudinal translation of the slidable tube moves the articulation arm to enable the loading unit 30 to articulate relative to the longitudinal axis "X-X" (FIG. 3). Reference may be made to U.S. Pat. Nos. 7,867, 252 and 8,282,670, and U.S. Patent Application Publication No. 2016/0166255, the entire contents of each of which are incorporated herein by reference, for a more detailed discussion of the structure and operation of a surgical tack applier including an articulation portion and a loading unit.

Figure 6:
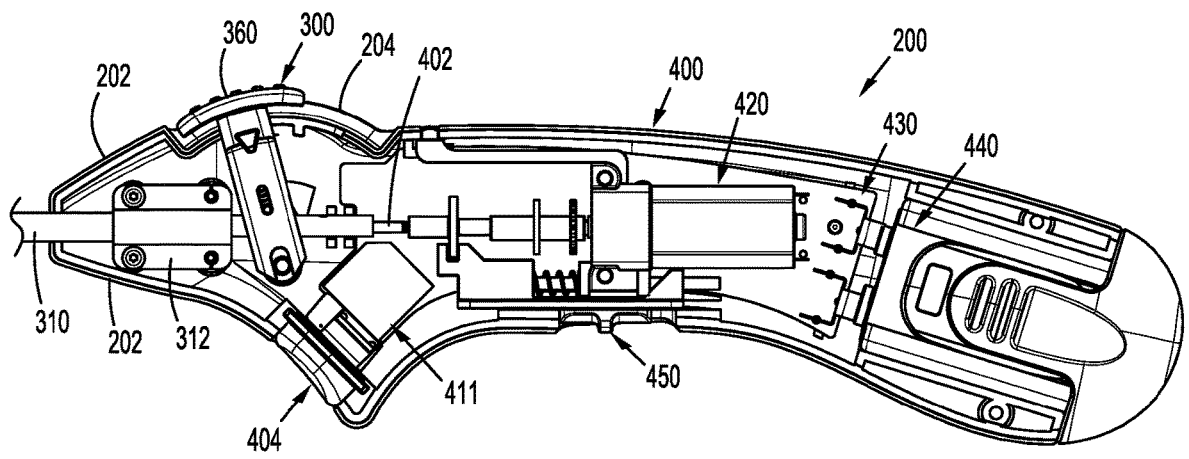
FIG. 6 is a side view of the handle assembly of FIG. 1 with a half of a housing removed.

With reference now to FIG. 6, the handle assembly 200 includes a housing 202, an articulation lever assembly 300 configured to articulate the articulation portion 60 (FIG. 2) of the elongate member 50, an actuation assembly 400 configured to eject the surgical tack 10 out of the loading unit 30 of the elongate member 50, and a battery pack 440 removably attached to the housing 202. The housing 202 includes an ergonomic structure providing comfort, ease of use, and intuitiveness such that when the housing 202 is gripped by a clinician, e.g., a thumb, may be positioned to slide the articulation lever assembly 300 and, e.g., an index finger, may be positioned to trigger an actuation switch 404 of the actuation assembly 400. Actuation of the actuation assembly 400 ejects a surgical tack 10 (FIG. 4) out of the loading unit 30 through mesh "M" (FIG. 4) and into body tissue "T".

Figure 7:
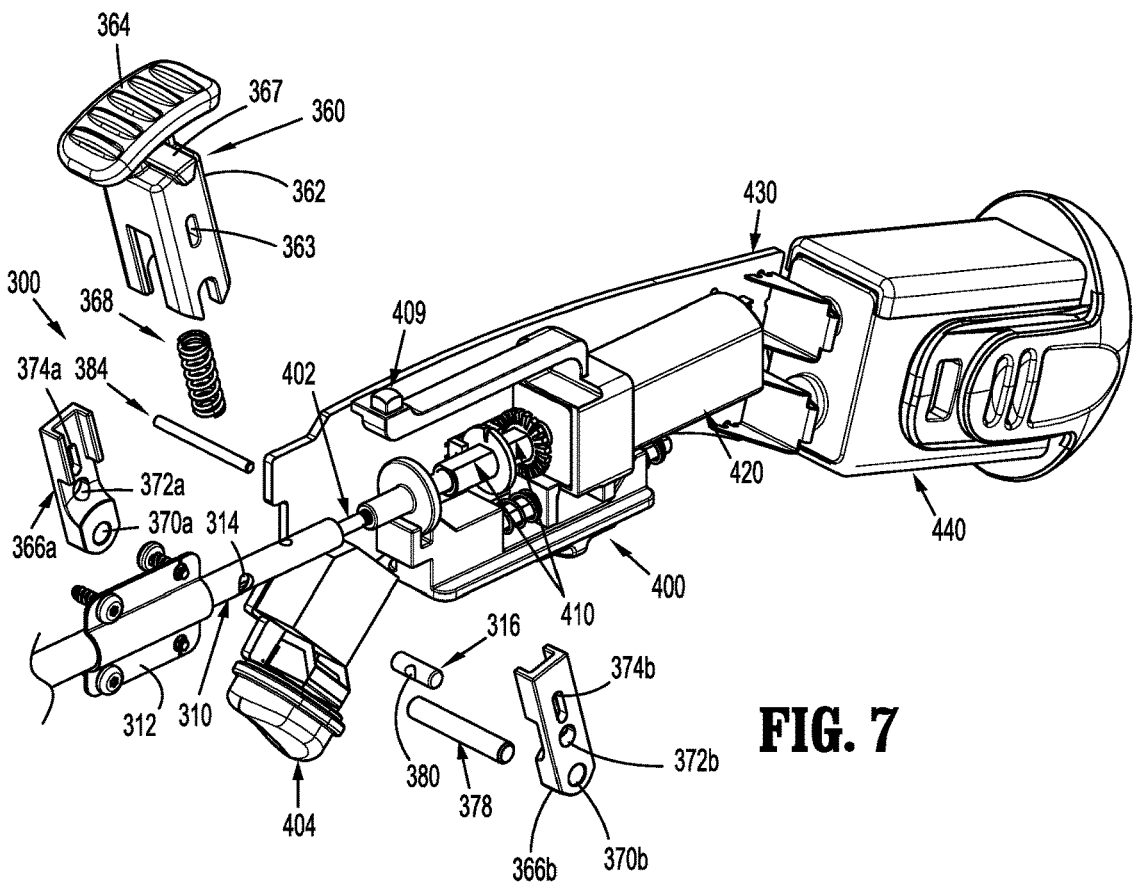
FIG. 7 is an exploded perspective view of the handle assembly of FIG. 1 with parts separated.

With reference to FIGS. 6 and 7, the articulation lever assembly 300 includes an articulation rod 310 and articulation lever 360 operatively coupled with the articulation rod 310. The articulation rod 310 is operatively coupled with the articulation portion 60 (FIG. 2) of the elongate member 50 of the surgical tack applier. The articulation rod 310 is slidably supported on the housing 202 of the handle assembly 200 by a mounting plate 312 defining a channel 304 (FIG. 8) configured to enable axial displacement of the articulation rod 310 therethrough, which, causes articulation of the articulation portion 60 (FIG. 2) based on the axial position of the articulation rod 310. In particular, the articulation rod 310 has an annular structure defining a channel 317 (FIG. 8) dimensioned to receive the actuation rod 402 of the actuation assembly 400 therein. The articulation rod 310 further defines a transverse bore 314 dimensioned to receive an articulation drive pin 316 coupled with the articulation lever 360.

With continued reference to FIGS. 6 and 7, the articulation lever 360 includes a housing portion 362 and an engaging portion 364 slidably engaging an engaging surface 204 of the housing 202. The engaging surface 204 has an arcuate profile enabling the engaging portion 364 to travel in, e.g., an arc. The housing portion 362 is disposed within the housing 202 and is dimensioned to receive articulation pivot arms 366a, 366b mated together to receive a biasing member 368 therebetween. Each articulation pivot arm 366a, 366b defines a first bore 370a, 370b, a second bore 372a, 372b, and a slot 374a, 374b. The first bores 370a, 370b are dimensioned to receive an articulation pivot pin 378 (FIG. 8) pivotably coupling the articulation pivot arms 366a, 366b to the housing 202. The second bores 372a, 372b are dimensioned to receive the articulation drive pin 316 extending through the transverse bore 314 of the articulation rod 310. Under such a configuration, when the articulation pivot arms 366a, 366b are pivoted about the articulation pivot pin 378, the articulation drive pin 316 causes axial displacement of the articulation rod 310. The articulation drive pin 316 defines a transverse bore 380 dimensioned to receive the actuation rod 402 of the actuation assembly 400 therethrough. The slots 374a, 374b of the articulation pivot arms 366a, 366b are dimensioned to cammingly receive a cam pin 384 biased away from the articulation pivot pin 378 by a biasing member 368 interposed between the articulation pivot arms 366a, 366b.

Figure 8:
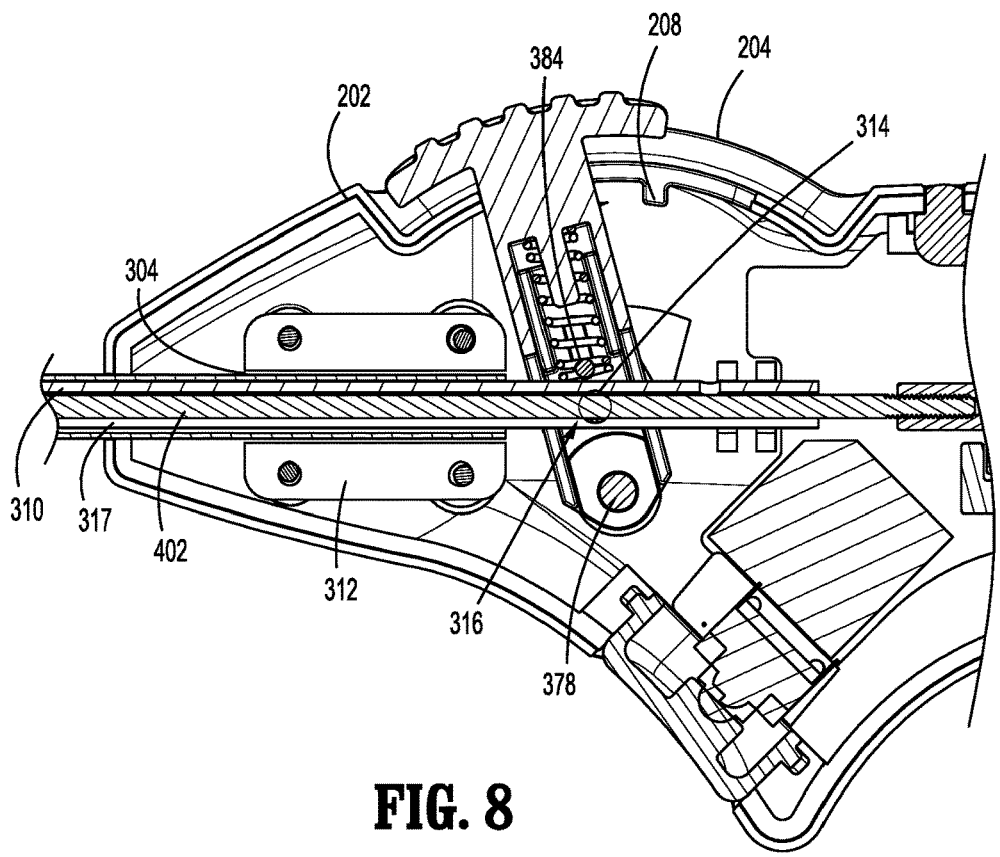
FIG. 8 is a partial side view of the handle assembly of FIG. 1.

With reference now to FIGS. 7 and 8, the housing portion 362 of the articulation lever 360 is dimensioned to receive the mated articulation pivot arms 366a, 366b. The housing portion 362 defines a slot 363 dimensioned to cammingly receive the cam pin 384 which is cammingly slidable in the slots 374a, 374b of the articulation pivot arms 366a, 366b. In addition, the housing portion 362 includes a tooth 367 configured to engage a detent portion 208 of the housing 202 to inhibit movement of the articulation lever 360 relative to the housing 202, thereby locking an axial position of the articulation rod 310, which, in turn, locks the orientation of the articulation portion 60 (FIG. 2) of the surgical tack applier. Under such a configuration, the articulation lever 360 is biased away from the articulation pivot pin 378 such that the tooth 367 of the housing portion 362 engages the detent portion 208. When the engaging portion 364 of the articulation lever 360 is depressed towards the housing 202, the tooth 367 is moved away from the detent portion 208 enabling the clinician to slidably move the engaging portion 364 on the engaging surface 204 (FIG. 6) of the housing 202, thereby enabling articulation of the articulation portion 60 of the surgical tack applier to a desired orientation.

Figure 9:
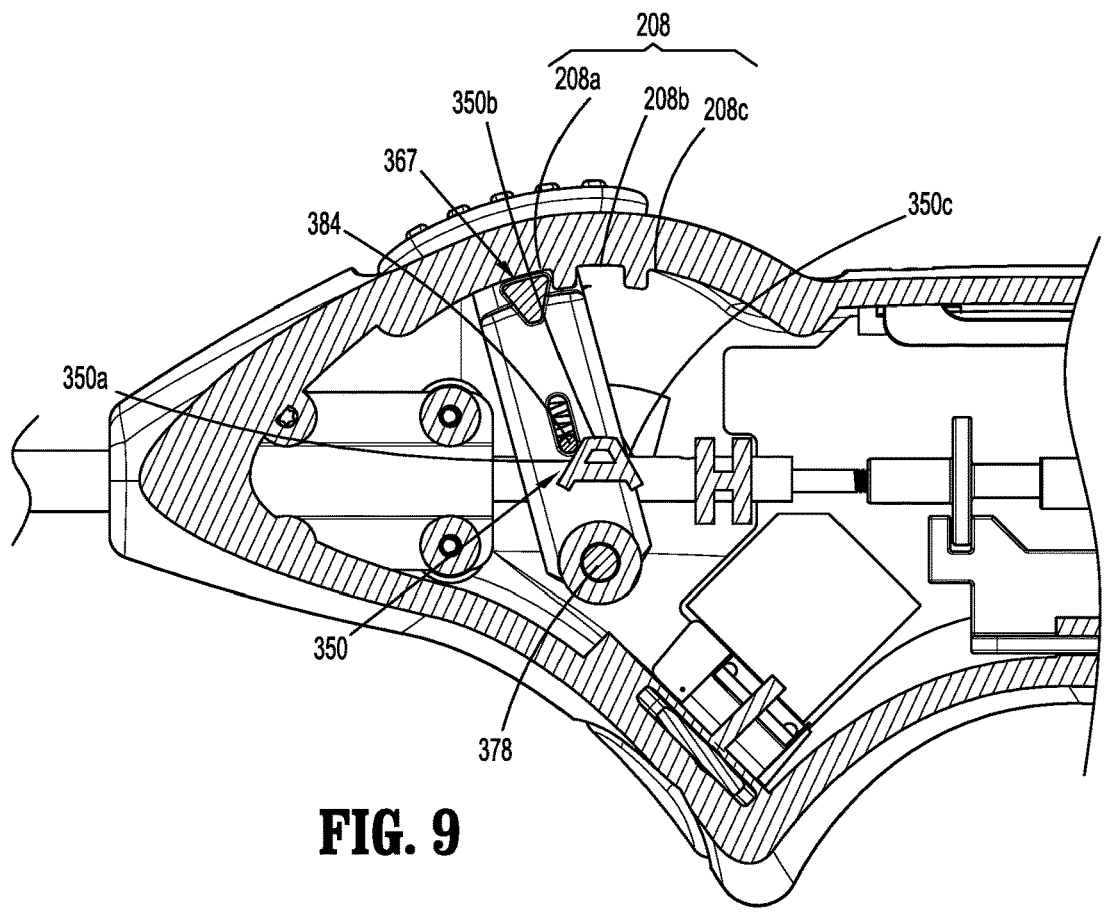
FIG. 9 is a partial side view of the handle assembly of FIG. 1 with a portion of the housing removed.

With reference now to FIG. 9 the articulation lever assembly 300 further includes a cam wedge 350 having first, second, and third portions 350a, 350b, 350c configured to cammingly engage the cam pin 384 which is cammingly slidable in the slots 374a, 374b of the articulation pivot arms 366a, 366b and the slot 363 of the articulation lever 360. The first, second, and third portions 350a, 350b, 350c correspond to the respective detent sections 208a, 208b, 208c of the detent portion 208. In this manner, articulation backlash is reduced as the cam pin 384 rides along the first, second, and third portions 350a, 350b, 350c of the cam wedge 350.

With reference back to FIGS. 6 and 7, the actuation assembly 400 includes an actuation rod 402 operatively coupled with the loading unit 30 (FIG. 2) of the surgical tack applier, a motor 420, an actuation switch 404 configured to actuate the motor 420 to eject the surgical tacks 10 (FIG. 4), a printed circuit board 430 including a microprocessor (not shown) to control the actuation assembly 400, and a battery pack 440 removably attached to the housing 202 and electrically connected to the motor 420 and the printed circuit board 430. A proximal end of the actuation rod 402 is operatively coupled with an output shaft of the motor 420 for concomitant rotation therewith such that when the actuation switch 404 is triggered by the clinician, the motor 420 is actuated to impart axial rotation to the actuation rod 402. A distal end of the actuation rod 402 is operatively coupled with the inner tube 38 (FIG. 3) of the loading unit 30 for concomitant rotation therewith.

Figure 4:
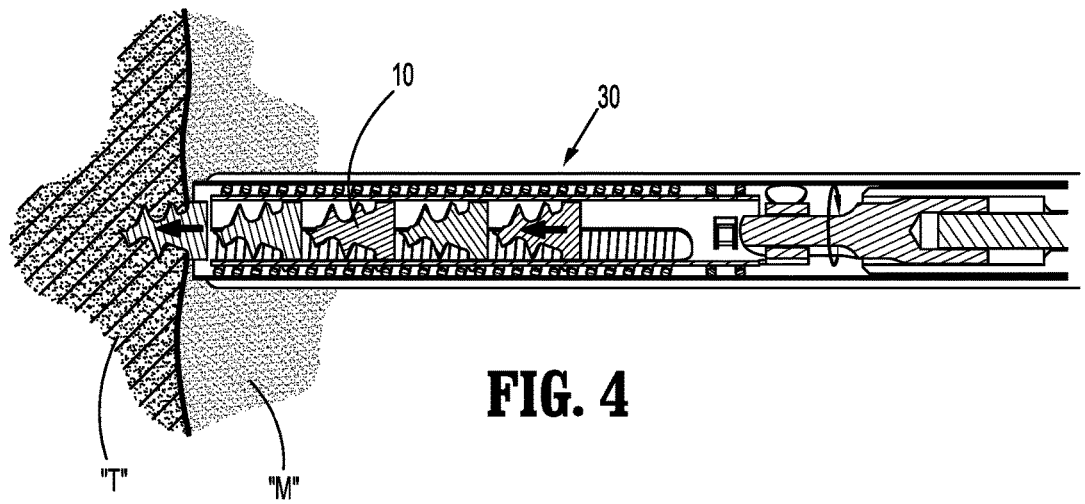
FIG. 4 is a longitudinal, cross-sectional view of a distal end of the powered surgical tack applier, illustrating implanting of a surgical tack into underlying tissue through a surgical mesh.
Figure 5:
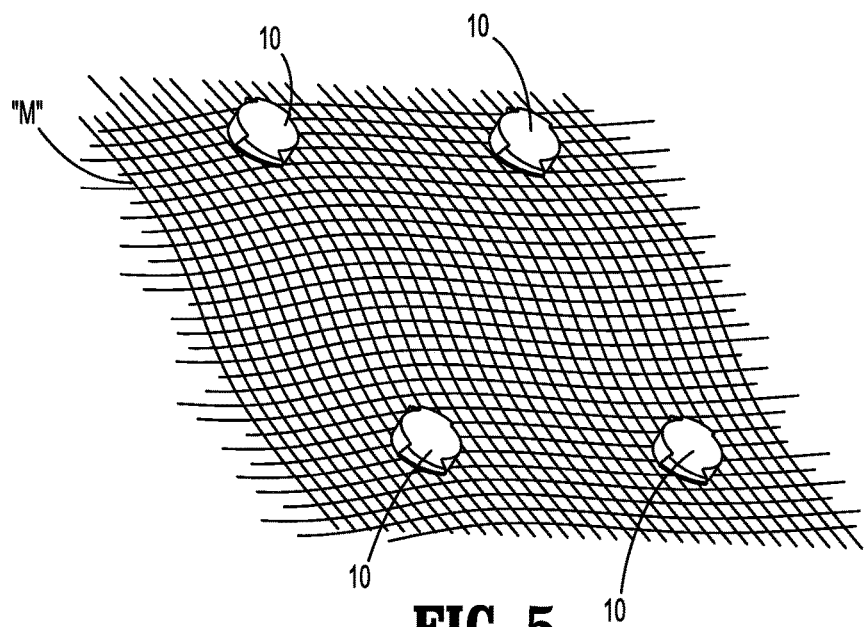
FIG. 5 is a perspective view of a surgical mesh for use with the powered surgical tack applier of FIG. 1, illustrating anchoring the surgical mesh to underlying tissue with a plurality of surgical tacks.
Figure 10:
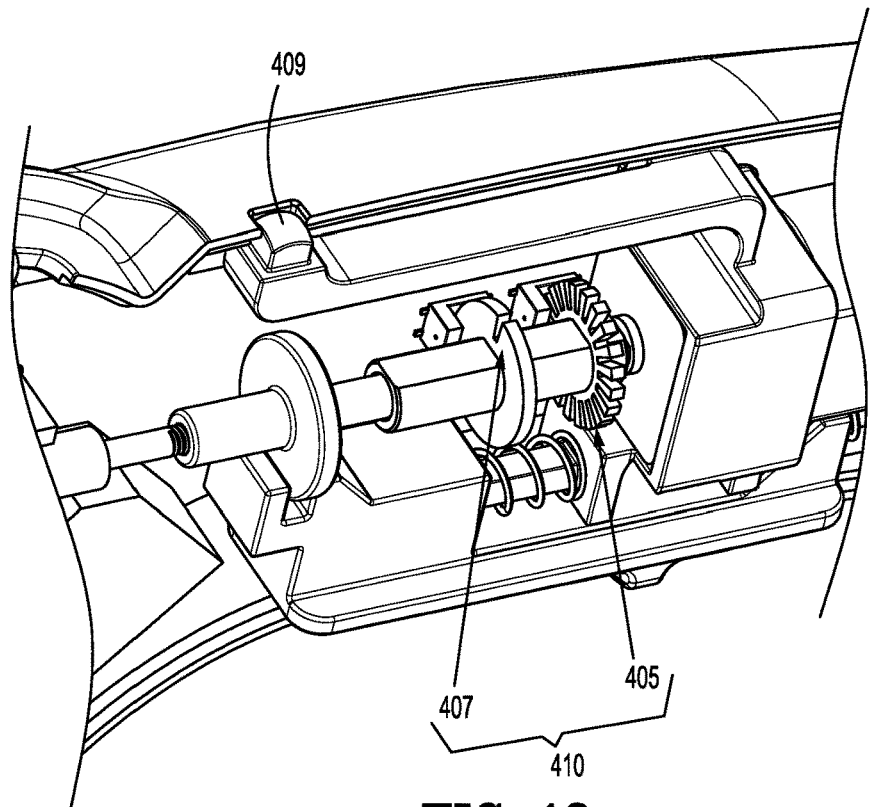
FIG. 10 is a partial perspective view of the handle assembly of FIG. 1, illustrating an actuation assembly.

With reference now to FIG. 10, the actuation assembly 400 may further include an encoder assembly 410 operatively connected to the actuation rod 402 and the processor of the printed circuit board 430. The encoder assembly 410 may include, e.g., an optical, motor encoder 405 configured to keep an accurate count of turns of the motor output shaft or the actuation rod 402 to ensure a proper number of turns are made to insert the surgical tack 10 through, e.g., the mesh "M", and into tissue "T" (FIG. 4). In addition, the encoder assembly 410 may further include, e.g., a single notched, encoder wheel 407 configured to ensure correct clocking of a distal end of the actuation rod 402 relative to the loading unit 30 (FIG. 2). The encoder assembly 410 may further include a light emitting diode ("LED") indicator 409 to indicate status of the ejection of each surgical tack 10. For example, a green light may indicate proper application of the surgical tact 10 through the mesh "M" and into tissue "T", and a red light may indicate, e.g., improper application of the surgical tack 10, due to an error signal from the optical motor encoder 405 or the single notched encoder wheel 407. Alternatively, the encoder assembly 410 may further include a piezoelectric element 411 (FIG. 6) for providing an audible tone for proper application of the surgical tack 10.

With brief reference to FIG. 6, the handle assembly 200 may further include a release lever 450 slidably attached to the housing 202. The release lever 450 is operatively coupled with the loading unit 30 (FIG. 2) such that when the release lever 450 is pulled, the loading unit 30 is detached from the elongate member 50 (FIG. 2) of the surgical tack applier.

Figure 11:
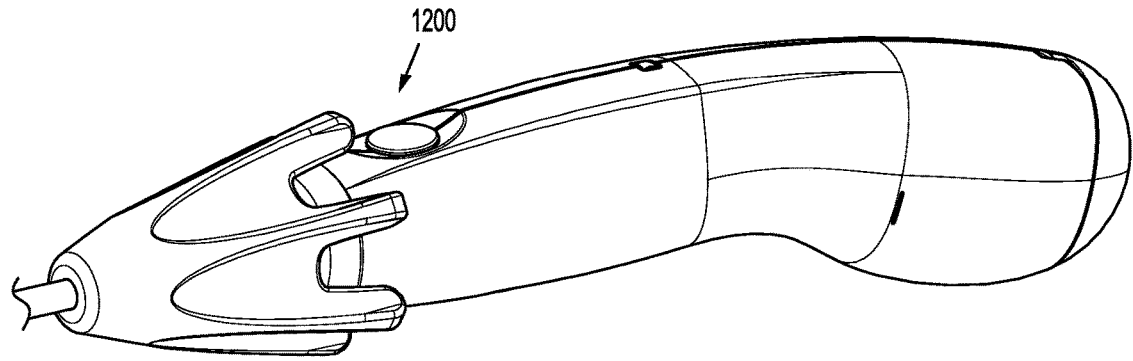
FIG. 11 is a perspective view of a handle assembly for use with a powered surgical tack applier in accordance with another embodiment of the present disclosure.
Figure 12:
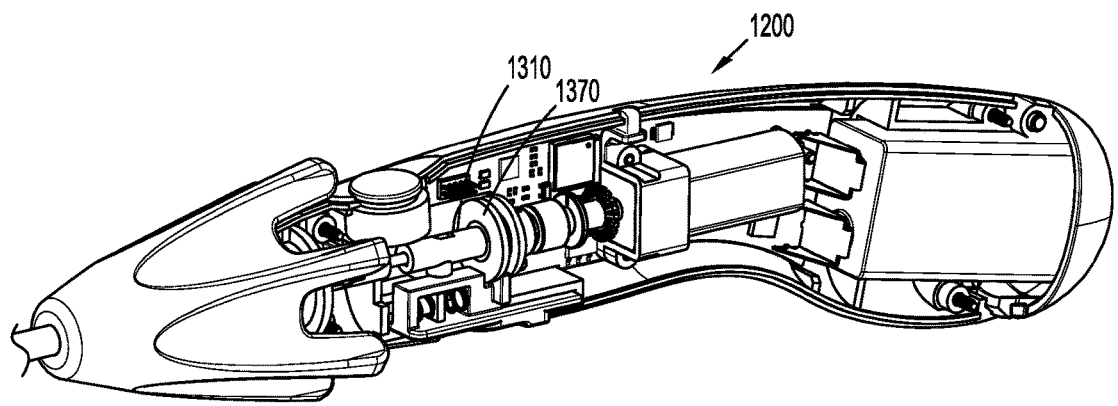
FIG. 12 is a perspective view of the handle assembly of FIG. 11 with a half of the housing removed.
Figure 13:
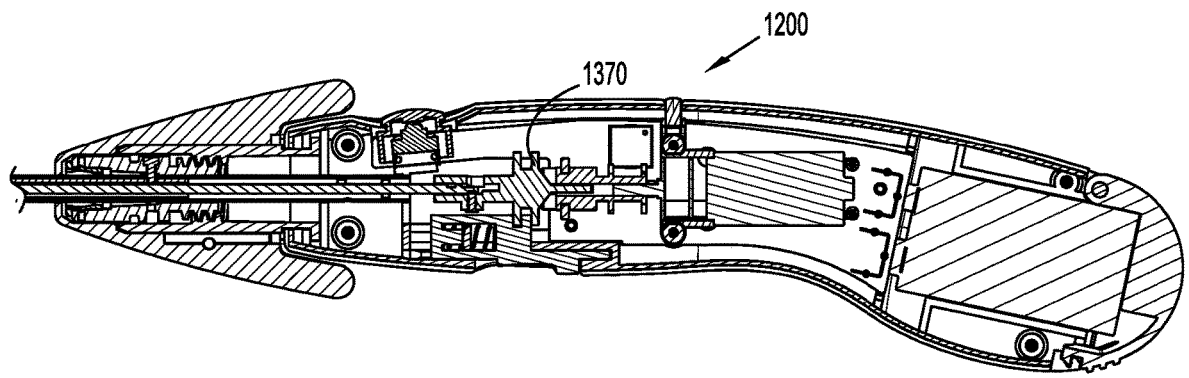
FIG. 13 is a side view of the handle assembly of FIG. 11.

In use, the loading unit 30 is operatively mounted to a distal end of the elongate member 50. The loading unit 30 is introduced into a target surgical site while in the non-articulated condition. The clinician may remotely articulate loading unit 30 relative the longitudinal axis "X-X" to access the surgical site. Specifically, the clinician may slide the engaging portion 364 of the articulation lever 360 along the engaging surface 204 of the housing 202. As the articulation rod 310 is displaced axially, the loading unit 30 is moved to an articulated orientation relative to the central longitudinal axis "X-X". Furthermore, the clinician may position the surgical mesh "M" adjacent the surgical site. Once the surgical mesh "M" is properly positioned on the surgical site, the clinician may trigger the actuation switch 404 to eject a surgical tack 10 through the mesh "M" and into tissue "T". While the actuation rod 310 is configured for axial displacement, it is further contemplated that an actuation rod 1310 may be rotatably supported by a rotor 1370 such that the actuation rod 1310 outputs an axial rotation which may be utilized by the loading unit 30 to effect articulation thereof, as can be appreciated with reference to FIGS. 11-13. It is further contemplated that the articulation assembly 400 may further include a transmission assembly to selectively impart rotation of the output shaft of the motor 420 to the actuation rod 1310.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A handle assembly for use with a surgical tack applier comprising:
   an actuation assembly including:
      a motor;
      an actuation rod having a first end operatively coupled to an output shaft of the motor for concomitant rotation therewith, and a second end operatively coupled to a loading unit of the surgical tack applier such that rotation of the actuation rod ejects a surgical tack from the loading unit;
      a piezoelectric element providing an audible tone for proper ejection of the surgical tack from the loading unit; and
      an actuation switch configured to actuate the motor; and
   an articulation lever assembly configured to articulate an articulation portion of the surgical tack applier, the articulation lever assembly including:
      an articulation rod operatively coupled with an articulation portion of the surgical tack applier such that axial displacement of the articulation rod causes articulation of the articulation portion; and
      an articulation lever operatively coupled with the articulation rod.

2. The handle assembly according to claim 1, wherein the actuation assembly further includes a processor configured to control the motor.

3. The handle assembly according to claim 2, wherein the actuation assembly further includes an optical motor encoder configured to count turns of the motor output shaft to ensure a proper number of turns are made to insert a surgical tack into tissue, the optical motor encoder operatively connected to the actuation rod and the processor.

4. The handle assembly according to claim 2, wherein the actuation assembly further includes an encoder wheel configured to ensure correct clocking of a distal end of the actuation rod relative to the loading unit.

5. The handle assembly according to claim 2, wherein the actuation assembly further includes a light emitting diode coupled with the processor to indicate status of ejection of the surgical tack from the loading unit.

6. The handle assembly according to claim 2, wherein the handle assembly further includes a battery pack electrically coupled to the motor and the processor.

7. The handle assembly according to claim 1, wherein the articulation rod defines a transverse bore dimensioned to receive a drive pin coupled with the articulation lever, the drive pin defining a bore dimensioned to receive the actuation rod therethrough.

8. The handle assembly according to claim 1, further comprising a housing pivotably supporting the articulation lever.

9. The handle assembly according to claim 8, wherein the articulation lever includes a housing portion and an engaging portion slidably disposed on an engaging surface of the housing.

10. The handle assembly according to claim 9, wherein the engaging surface defines an arcuate profile to enable sliding of the engaging portion in an arc.

11. The handle assembly according to claim 10, wherein the articulation lever assembly includes a biasing member configured to bias the engaging portion of the articulation lever away from the housing of the handle assembly.

12. The handle assembly according to claim 11, wherein the housing includes a detent portion configured to secure a position of the articulation lever relative to the housing of the handle assembly.

13. The handle assembly according to claim 11, wherein the articulation lever assembly further includes articulation pivot arms pivotably secured to the housing of the handle assembly, the articulation pivot arms configured to receive the biasing member therebetween.

14. The handle assembly according to claim 13, wherein the articulation pivot arms are received in the housing portion of the articulation lever.

15. The handle assembly according to claim 8, wherein the articulation rod defines a lumen dimensioned to receive the actuation rod therethrough.

16. A surgical tack applier comprising:
   a handle assembly comprising:
      a housing;
      an actuation assembly including:
         a motor;
         an actuation rod having a first end operatively coupled to an output shaft of the motor for concomitant rotation therewith; and
         an actuation switch configured to actuate the motor; and
      an articulation lever assembly including:
         an articulation rod;

an articulation lever operatively coupled with the articulation rod; and articulation pivot arms pivotably secured to the housing of the handle assembly, the articulation pivot arms configured to receive a biasing member therebetween; and an elongate member extending distally from the handle assembly, the elongate member including a loading unit having a plurality of surgical tacks, and an articulation portion configured to pivot with respect to a longitudinal axis defined by the elongate member, wherein the articulation rod is operatively coupled with the articulation portion of the elongate member such that axial displacement of the articulation rod causes articulation of the articulation portion, and a second end of the actuation rod operatively coupled to the loading unit such that rotation of the actuation rod ejects a surgical tack from the loading unit, the actuation rod extending through the articulation rod.

17. The surgical tack applier according to claim 16, wherein the actuation assembly further includes a processor configured to control the motor.

18. The surgical tack applier according to claim 17, wherein the actuation assembly further includes an optical motor encoder configured to count required turns of the motor output shaft to ensure a proper number of turns are made to insert a surgical tack into tissue, the optical motor encoder operatively connected to the actuation rod and the processor.

19. The surgical tack applier according to claim 18, wherein the actuation assembly further includes an encoder wheel configured to ensure correct clocking of a distal end of the actuation rod relative to the loading unit.

20. A handle assembly for use with a surgical tack applier comprising:

a housing including an engaging surface defining an arcuate profile;

an actuation assembly including:

a motor;

an actuation rod having a first end operatively coupled to an output shaft of the motor for concomitant rotation therewith, and a second end operatively coupled to a loading unit of the surgical tack applier such that rotation of the actuation rod ejects a surgical tack from the loading unit; and an actuation switch configured to actuate the motor; and an articulation lever assembly configured to articulate an articulation portion of the surgical tack applier, the articulation lever assembly including:

an articulation rod operatively coupled with an articulation portion of the surgical tack applier such that axial displacement of the articulation rod causes articulation of the articulation portion;

an articulation lever operatively coupled with the articulation rod, the articulation lever including a housing portion and an engaging portion slidably disposed on the engaging surface of the housing, the arcuate profile enabling sliding of the engaging portion in an arc;

a biasing member configured to bias the engaging portion of the articulation lever away from the housing of the handle assembly; and articulation pivot arms pivotably secured to the housing of the handle assembly, the articulation pivot arms configured to receive the biasing member therebetween.

21. The handle assembly according to claim 20, wherein the articulation pivot arms are received in the housing portion of the articulation lever.

22. The handle assembly according to claim 20, wherein the housing includes a detent portion configured to secure a position of the articulation lever relative to the housing of the handle assembly.

* * * * *